US007335350B2

(12) United States Patent
Proudfoot et al.

(10) Patent No.: US 7,335,350 B2
(45) Date of Patent: Feb. 26, 2008

(54) CHEMOKINES MUTANTS HAVING IMPROVED ORAL BIOAVAILABILITY

(75) Inventors: Amanda Proudfoot, Chens sur Leman (FR); Marie Kosco-Vilbois, Minzier (FR); Timothy Wells, Prevessin Moens (FR)

(73) Assignee: Laboratoires Serono SA, Coinsins, Vaud (CH)

( * ) Notice: Subject to any disclaimer, the term of this patent is extended or adjusted under 35 U.S.C. 154(b) by 0 days.

(21) Appl. No.: 10/510,014

(22) PCT Filed: Mar. 31, 2003

(86) PCT No.: PCT/EP03/50084

§ 371 (c)(1),
(2), (4) Date: Apr. 11, 2005

(87) PCT Pub. No.: WO03/084562

PCT Pub. Date: Oct. 16, 2003

(65) Prior Publication Data

US 2005/0220759 A1 Oct. 6, 2005

(30) Foreign Application Priority Data

Apr. 4, 2002 (EP) .................................. 02100339

(51) Int. Cl.
*A61K 45/00* (2006.01)
*A61K 39/00* (2006.01)
*A01N 37/18* (2006.01)

(52) U.S. Cl. ...................... 424/85.1; 424/185.1; 514/2
(58) Field of Classification Search ..................... None
See application file for complete search history.

(56) References Cited

U.S. PATENT DOCUMENTS

| 5,854,412 | A | | 12/1998 | Rollins et al. |
| 5,871,723 | A | * | 2/1999 | Strieter et al. ............. 424/85.1 |
| 5,965,697 | A | | 10/1999 | Czaplewski et al. |
| 6,214,940 | B1 | | 4/2001 | DeVico et al. |
| 6,316,420 | B1 | | 11/2001 | Karin et al. |

FOREIGN PATENT DOCUMENTS

| WO | WO 98/06751 | | 2/1998 |
| WO | WO 99/33989 | * | 7/1999 |
| WO | WO 00/44408 | | 8/2000 |
| WO | WO 02/28419 | | 4/2002 |

OTHER PUBLICATIONS

Proudfoot, A.E.I, et al. 2001. The BBXB motif of RANTES is the principal site for heparin binding and controls receptor selectivity. J. Biol. Chem. vol. 276, p. 10620-10626. Published online Dec. 14, 2000.*
Schall, T.J. et al. 1988. A human T cell-specific molecule is a member of a new gene family. J. Immunol. vol. 141, p. 1018-1025.*
Luck, D.N., et al. 1991. Single amino acid substitutuions in recombinant bovine prolactin that markedly reduce its mitogenic activity in Nb2 cell cultures. Mol. Endocrinol. vol. 5(12), p. 1880-1886.*
Koopmann, W. et al. "Identification of a Glycosaminoglycan-Binding Site in Chemokine Macrophage Inflammatory Protein-1α" *The Journal of Biological Chemistry*, Apr. 11, 1997, pp. 10103-10109, vol. 272, No. 15.
Koopmann, W. et al. "Structure and Function of the Glycosaminoglycan Binding Site of Chemokine Macrophage-Inflammatory Protein-1β" *The Journal of Immunology*, 1999, pp. 2120-2127, vol. 163.
Kuschert, G. S. V. et al. "Glycosaminoglycans Interact Selectively with Chemokines and Modulate Receptor Binding and Cellular Responses" *Biochemistry*, 1999, pp. 12959-12968, vol. 38.
Appay, V. et al. "Aggregation of RANTES is Responsible for Its Inflammatory Properties", *The Journal of Biological Chemistry*, Sep. 24, 1999, pp. 27505-27512, vol. 274, No. 39.
Czaplewski, L. et al. "Identification of Amino Acid Residues Critical for Aggregation of Human CC Chemokines Macrophage Inflammatory Protein (MIP)-1α, MIP-1β, and RANTES", *The Journal of Biological Chemistry*, Jun. 4, 1999, pp. 16077-16084, vol. 274, No. 23.
Fritchley, S.J. et al. "Identification of Heparan Sulphate Binding Site In Rantes: Consequences For Leukocyte Activation", *Immunology*, Dec. 1999, p. 47, (Joint Congress of the British Society for Immunology and the British Society for Allergy & Clinical Immunology, Harrogate, England, UK); vol. 98, No. Suppl. 1, XP-001010396.
Graham, G. et al. "Uncoupling of stem cell inhibition from monocyte chemoattraction in the MIP-1α by mutagenesis of the proteoglycan binding site", *The EMBO Journal*, 1996, pp. 6506-6515, (Oxford University Press); vol. 15, No. 23, XP-002173221.
Hoogewerf, A. et al. "Glycosaminoglycans Mediate Cell Surface Oligomerization of Chemokines", *Biochemistry*, 1997, pp. 13570-13578, vol. 36.
Laurence, J. et al. "Importance of Basic Residues and Quarternary Structure in the Function of MIP-1β: CCR5 Binding and Cell Surface Sugar Interactions", *Biochemistry*, Apr. 24, 2001, pp. 4990-4999, vol. 40, No. 16, XP-002193384.
Proudfoot, A. "Probing the role of the GAC/Chemokine interaction", Chemokine Gordon Conference (Session I, Jul. 24, 2000).
Proudfoot, A. et al. "The BBXB Motif of RANTES Is the Principal Site for Heparin Binding and Controls Receptor Selectivity", *The Journal of Biological Chemistry*, Apr. 6, 2001, pp. 10620-10626, vol. 276, No. 14.
Schwartz, M. and Wells, T.N.C. "Interfering with Chemokine networks—the hope for new therapeutics", *Current Opinion in Chemical Biology*, 1999, pp. 407-417, vol. 3.
Johnson, Z. "Interference with Heparin Binding and Oligomerization Creates a Novel Anti-Inflammatory Strategy Targeting the Chemokine System" *The Journal of Immunology*, 2004, pp. 5776-5785, vol. 173.
Johnson, Z. "The Role of Glycosaminoglycan Binding and Olimerisation in Chemokine Function in Vivo" Thesis submitted for the Degree of Doctor of Philosophy, University of London, Nov. 2003, pp. 1-273.

* cited by examiner

*Primary Examiner*—Robert Landsman
*Assistant Examiner*—Bruce D. Hissong
(74) *Attorney, Agent, or Firm*—Saliwanchik, Lloyd & Saliwanchik

(57) ABSTRACT

The oral efficacy of C—C chemokines containing a dibasic site in the 40's conserved cationic sequence, such as RANTES and MIP-1β, is improved by substituting at least one of the residues in the dibasic site in a non-conservative manner.

3 Claims, 4 Drawing Sheets

A)

B)

SEQUENCE LISTING

```
<160> NUMBER OF SEQ ID NOS: 15

<210> SEQ ID NO 1
<211> LENGTH: 91
<212> TYPE: PRT
<213> ORGANISM: Escherichia coli
<220> FEATURE:
<221> NAME/KEY: mat_peptide
<222> LOCATION: (1)..(68)
<223> OTHER INFORMATION: carboxy terminal amino acid

<400> SEQUENCE: 1

Met Lys Val Ser Ala Ala Ala Leu Ala Val Ile Leu Ile Ala Thr Ala
            -20                 -15                 -10

Leu Cys Ala Pro Ala Ser Ala Ser Pro Tyr Ser Ser Asp Thr Thr Pro
        -5              -1   1               5
```

```
Cys Cys Phe Ala Tyr Ile Ala Arg Pro Leu Pro Arg Ala His Ile Lys
 10              15                  20                  25

Glu Tyr Phe Tyr Thr Ser Gly Lys Cys Ser Asn Pro Ala Val Val Phe
                 30                  35                  40

Val Thr Ala Ala Asn Ala Gln Val Cys Ala Asn Pro Glu Lys Lys Trp
                 45                  50                  55

Val Arg Glu Tyr Ile Asn Ser Leu Glu Met Ser
         60                  65
```

<210> SEQ ID NO 2
<211> LENGTH: 66
<212> TYPE: PRT
<213> ORGANISM: Escherichia coli

<400> SEQUENCE: 2

```
Tyr Ser Ser Asp Thr Thr Pro Cys Cys Phe Ala Tyr Ile Ala Arg Pro
 1               5                  10                  15

Leu Pro Arg Ala His Ile Lys Glu Tyr Phe Tyr Thr Ser Gly Lys Cys
                 20                  25                  30

Ser Asn Pro Ala Val Val Phe Val Thr Ala Ala Asn Ala Gln Val Cys
                 35                  40                  45

Ala Asn Pro Glu Lys Lys Trp Val Arg Glu Tyr Ile Asn Ser Leu Glu
         50                  55                  60

Met Ser
 65
```

<210> SEQ ID NO 3
<211> LENGTH: 92
<212> TYPE: PRT
<213> ORGANISM: Escherichia coli
<220> FEATURE:
<221> NAME/KEY: mat_peptide
<222> LOCATION: (1)..(69)
<223> OTHER INFORMATION: carboxy terminal amino acid

<400> SEQUENCE: 3

```
Met Lys Val Ser Ala Ala Ala Leu Ala Val Ile Leu Ile Ala Thr Ala
         -20                 -15                 -10

Leu Cys Ala Pro Ala Ser Ala Met Ser Pro Tyr Ser Ser Asp Thr Thr
         -5                  -1  1                   5

Pro Cys Cys Phe Ala Tyr Ile Ala Arg Pro Leu Pro Arg Ala His Ile
 10                  15                  20                  25

Lys Glu Tyr Phe Tyr Thr Ser Gly Lys Cys Ser Asn Pro Ala Val Val
                 30                  35                  40

Phe Val Thr Ala Ala Asn Ala Gln Val Cys Ala Asn Pro Glu Lys Lys
                 45                  50                  55

Trp Val Arg Glu Tyr Ile Asn Ser Leu Glu Met Ser
         60                  65
```

<210> SEQ ID NO 4
<211> LENGTH: 91
<212> TYPE: PRT
<213> ORGANISM: Escherichia Coli
<220> FEATURE:
<221> NAME/KEY: mat_peptide
<222> LOCATION: (1)..(68)
<223> OTHER INFORMATION: carboxy terminal amino acid

<400> SEQUENCE: 4

```
Met Lys Val Ser Ala Ala Ala Leu Ala Val Ile Leu Ile Ala Thr Ala
         -20                 -15                 -10
```

```
Leu Cys Ala Pro Ala Ser Ala Ser Pro Tyr Ser Ser Asp Thr Thr Pro
        -5              -1  1                   5

Cys Cys Phe Ala Tyr Ile Ala Arg Pro Leu Pro Arg Ala His Ile Lys
 10               15              20                      25

Glu Tyr Phe Tyr Thr Ser Asn Lys Cys Ser Asn Pro Ala Val Val Phe
                 30              35                  40

Val Thr Ala Ala Asn Ala Gln Val Cys Ala Asn Pro Glu Lys Lys Trp
             45              50              55

Val Arg Glu Tyr Ile Asn Ser Leu Glu Met Ser
         60              65
```

```
<210> SEQ ID NO 5
<211> LENGTH: 68
<212> TYPE: PRT
<213> ORGANISM: Escherichia coli

<400> SEQUENCE: 5

Ser Pro Tyr Ser Ser Asp Thr Thr Pro Cys Cys Phe Ala Tyr Ile Ala
 1                5              10                  15

Arg Pro Leu Pro Arg Ala His Ile Lys Glu Tyr Phe Tyr Thr Ser Gly
             20              25                  30

Lys Cys Ser Asn Pro Ala Val Val Phe Val Thr Arg Glu Asn Arg Gln
         35              40                  45

Val Cys Ala Asn Pro Glu Lys Lys Trp Val Arg Glu Tyr Ile Asn Ser
     50              55                  60

Leu Glu Met Ser
 65
```

```
<210> SEQ ID NO 6
<211> LENGTH: 92
<212> TYPE: PRT
<213> ORGANISM: Escherichia coli
<220> FEATURE:
<221> NAME/KEY: mat_peptide
<222> LOCATION: (1)..(69)
<223> OTHER INFORMATION: carboxy terminal amino acid

<400> SEQUENCE: 6

Met Lys Val Ser Ala Ala Ala Leu Ala Val Ile Leu Ile Ala Thr Ala
         -20             -15                 -10

Leu Cys Ala Pro Ala Ser Ala Met Ser Pro Tyr Ser Ser Asp Thr Thr
        -5              -1  1                   5

Pro Cys Cys Phe Ala Tyr Ile Ala Arg Pro Leu Pro Arg Ala His Ile
 10              15              20                      25

Lys Glu Tyr Phe Tyr Thr Ser Asn Lys Cys Ser Asn Pro Ala Val Val
                 30              35                  40

Phe Val Thr Arg Lys Asn Arg Gln Val Cys Ala Asn Pro Glu Lys Lys
             45              50              55

Trp Val Arg Glu Tyr Ile Asn Ser Leu Glu Met Ser
         60              65
```

```
<210> SEQ ID NO 7
<211> LENGTH: 89
<212> TYPE: PRT
<213> ORGANISM: Escherichia coli
<220> FEATURE:
<221> NAME/KEY: mat_peptide
<222> LOCATION: (1)..(66)
<223> OTHER INFORMATION: carboxy terminal amino acid
```

<400> SEQUENCE: 7

Met Lys Val Ser Ala Ala Ala Leu Ala Val Ile Leu Ile Ala Thr Ala
            -20                 -15                 -10

Leu Cys Ala Pro Ala Ser Ala Tyr Ser Ser Asp Thr Thr Pro Cys Cys
         -5              -1   1               5

Phe Ala Tyr Ile Ala Arg Pro Leu Pro Arg Ala His Ile Lys Glu Tyr
 10              15                  20                  25

Phe Tyr Thr Ser Asn Lys Cys Ser Asn Pro Ala Val Val Phe Val Thr
             30                  35                  40

Arg Lys Asn Arg Gln Val Cys Ala Asn Pro Glu Lys Lys Trp Val Arg
             45                  50                  55

Glu Tyr Ile Asn Ser Leu Glu Met Ser
         60                  65

<210> SEQ ID NO 8
<211> LENGTH: 70
<212> TYPE: PRT
<213> ORGANISM: Escherichia coli

<400> SEQUENCE: 8

Ala Ser Leu Ala Ala Asp Thr Pro Thr Ala Cys Cys Phe Ser Tyr Thr
 1               5                  10                  15

Ser Ala Gln Ile Pro Gln Asn Phe Ile Ala Asp Tyr Phe Glu Thr Ser
             20                  25                  30

Ser Gln Cys Ser Lys Pro Gly Val Ile Phe Leu Thr Lys Ala Ser Ala
             35                  40                  45

Gln Val Cys Ala Asp Pro Ser Glu Glu Trp Val Gln Lys Tyr Val Ser
         50                  55                  60

Asp Leu Glu Leu Ser Ala
 65                  70

<210> SEQ ID NO 9
<211> LENGTH: 69
<212> TYPE: PRT
<213> ORGANISM: Escherichia coli

<400> SEQUENCE: 9

Ala Pro Met Gly Ser Asp Pro Pro Thr Ala Cys Cys Phe Ser Tyr Thr
 1               5                  10                  15

Ala Arg Lys Leu Pro Arg Asn Phe Val Val Asp Tyr Tyr Glu Thr Ser
             20                  25                  30

Ser Leu Cys Ser Gln Pro Ala Val Val Phe Gln Thr Ala Ala Ser Ala
             35                  40                  45

Gln Val Cys Ala Asp Pro Ser Glu Ser Trp Val Gln Glu Tyr Val Tyr
         50                  55                  60

Asp Leu Glu Leu Asn
 65

<210> SEQ ID NO 10
<211> LENGTH: 91
<212> TYPE: PRT
<213> ORGANISM: Escherichia coli
<220> FEATURE:
<221> NAME/KEY: SIGNAL
<222> LOCATION: (1)..(23)
<223> OTHER INFORMATION: carboxy terminal amino acid

<400> SEQUENCE: 10

Met Lys Val Ser Ala Ala Ala Leu Ala Val Ile Leu Ile Ala Thr Ala

```
                 1               5                  10                 15
Leu Cys Ala Pro Ala Ser Ala Ser Pro Tyr Ser Ser Asp Thr Thr Pro
                20                  25                 30

Cys Cys Phe Ala Tyr Ile Ala Arg Pro Leu Pro Arg Ala His Ile Lys
                35                  40                 45

Glu Tyr Phe Tyr Thr Ser Gly Lys Cys Ser Asn Pro Ala Val Val Phe
                50                  55                 60

Val Thr Arg Lys Asn Arg Gln Val Cys Ala Asn Pro Glu Lys Lys Trp
 65                 70                  75                 80

Val Arg Glu Tyr Ile Asn Ser Leu Glu Met Ser
                85                  90

<210> SEQ ID NO 11
<211> LENGTH: 92
<212> TYPE: PRT
<213> ORGANISM: Escherichia coli
<220> FEATURE:
<221> NAME/KEY: mat_peptide
<222> LOCATION: (1)..(69)
<223> OTHER INFORMATION: carboxy terminal amino acid

<400> SEQUENCE: 11

Met Lys Val Ser Ala Ala Ala Leu Ala Val Ile Leu Ile Ala Thr Ala
                -20                 -15                -10

Leu Cys Ala Pro Ala Ser Ala Met Ser Pro Tyr Ser Ser Asp Thr Thr
                -5                  -1   1              5

Pro Cys Cys Phe Ala Tyr Ile Ala Arg Pro Leu Pro Arg Ala His Ile
 10                 15                  20                 25

Lys Glu Tyr Phe Tyr Thr Ser Gly Lys Cys Ser Asn Pro Ala Val Val
                30                  35                 40

Phe Val Thr Arg Lys Asn Lys Gln Val Cys Ala Asn Pro Glu Lys Lys
                45                  50                 55

Trp Val Arg Glu Tyr Ile Asn Ser Leu Glu Met Ser
                60                  65

<210> SEQ ID NO 12
<211> LENGTH: 89
<212> TYPE: PRT
<213> ORGANISM: Pichia Pastoris
<220> FEATURE:
<221> NAME/KEY: mat_peptide
<222> LOCATION: (1)..(66)
<223> OTHER INFORMATION: carboxy terminal amino acid

<400> SEQUENCE: 12

Met Lys Val Ser Ala Ala Ala Leu Ala Val Ile Leu Ile Ala Thr Ala
                -20                 -15                -10

Leu Cys Ala Pro Ala Ser Ala Tyr Ser Ser Asp Thr Thr Pro Cys Cys
                -5                  -1   1              5

Phe Ala Tyr Ile Ala Arg Pro Leu Pro Arg Ala His Ile Lys Glu Tyr
 10                 15                  20                 25

Phe Tyr Thr Ser Gly Lys Cys Ser Asn Pro Ala Val Val Phe Val Thr
                30                  35                 40

Arg Lys Asn Arg Gln Val Cys Ala Asn Pro Glu Lys Lys Trp Val Arg
                45                  50                 55

Glu Tyr Ile Asn Ser Leu Glu Met Ser
                60                  65

<210> SEQ ID NO 13
```

```
<211> LENGTH: 91
<212> TYPE: PRT
<213> ORGANISM: Escherichia Coli
<220> FEATURE:
<221> NAME/KEY: mat_peptide
<222> LOCATION: (1)..(68)
<223> OTHER INFORMATION: carboxy terminal amino acid

<400> SEQUENCE: 13

Met Lys Val Ser Ala Ala Ala Leu Ala Val Ile Leu Ile Ala Thr Ala
            -20                 -15                 -10

Leu Cys Ala Pro Ala Ser Ala Ser Pro Tyr Ser Ser Asp Thr Thr Pro
        -5                  -1   1                   5

Cys Cys Phe Ala Tyr Ile Ala Arg Pro Leu Pro Arg Ala His Ile Lys
 10                  15                  20                  25

Glu Tyr Phe Tyr Thr Ser Asn Lys Cys Ser Asn Pro Ala Val Val Phe
                 30                  35                  40

Val Thr Arg Lys Asn Arg Gln Val Cys Ala Asn Pro Glu Lys Lys Trp
             45                  50                  55

Val Arg Glu Tyr Ile Asn Ser Leu Glu Met Ser
             60                  65

<210> SEQ ID NO 14
<211> LENGTH: 70
<212> TYPE: PRT
<213> ORGANISM: Escherichia coli

<400> SEQUENCE: 14

Ala Ser Leu Ala Ala Asp Thr Pro Thr Ala Cys Cys Phe Ser Tyr Thr
 1               5                  10                  15

Ser Arg Gln Ile Pro Gln Asn Phe Ile Ala Asp Tyr Phe Glu Thr Ser
             20                  25                  30

Ser Gln Cys Ser Lys Pro Gly Val Ile Phe Leu Thr Lys Arg Ser Arg
         35                  40                  45

Gln Val Cys Ala Asp Pro Ser Glu Glu Trp Val Gln Lys Tyr Val Ser
     50                  55                  60

Asp Leu Glu Leu Ser Ala
 65                  70

<210> SEQ ID NO 15
<211> LENGTH: 69
<212> TYPE: PRT
<213> ORGANISM: Escherichia coli

<400> SEQUENCE: 15

Ala Pro Met Gly Ser Asp Pro Pro Thr Ala Cys Cys Phe Ser Tyr Thr
 1               5                  10                  15

Ala Arg Lys Leu Pro Arg Asn Phe Val Val Asp Tyr Tyr Glu Thr Ser
             20                  25                  30

Ser Leu Cys Ser Gln Pro Ala Val Val Phe Gln Thr Lys Arg Ser Lys
         35                  40                  45

Gln Val Cys Ala Asp Pro Ser Glu Ser Trp Val Gln Glu Tyr Val Tyr
     50                  55                  60

Asp Leu Glu Leu Asn
 65
```

CHEMOKINES MUTANTS HAVING IMPROVED ORAL BIOAVAILABILITY

CROSS-REFERENCE TO RELATED APPLICATION

Figure 1:
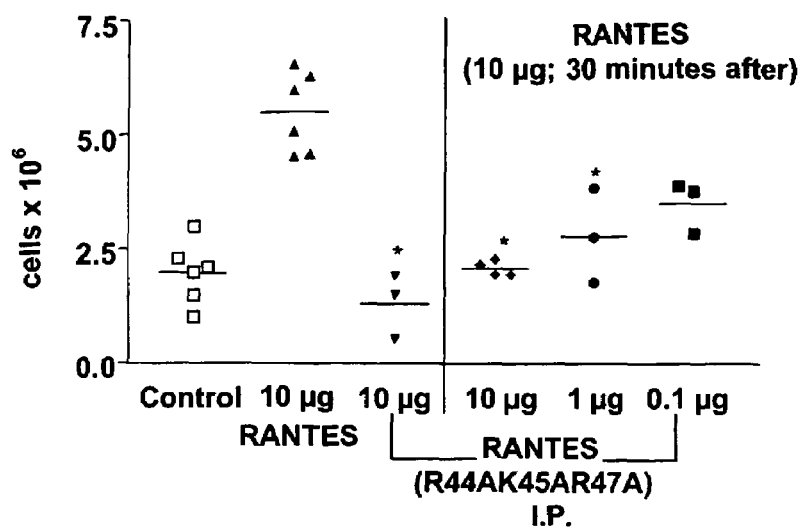
Figure 1:
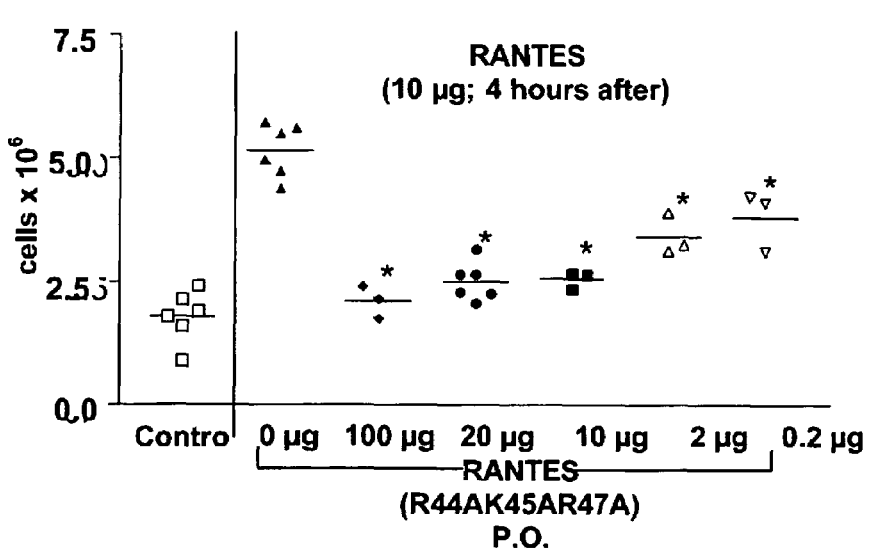
Figure 1:
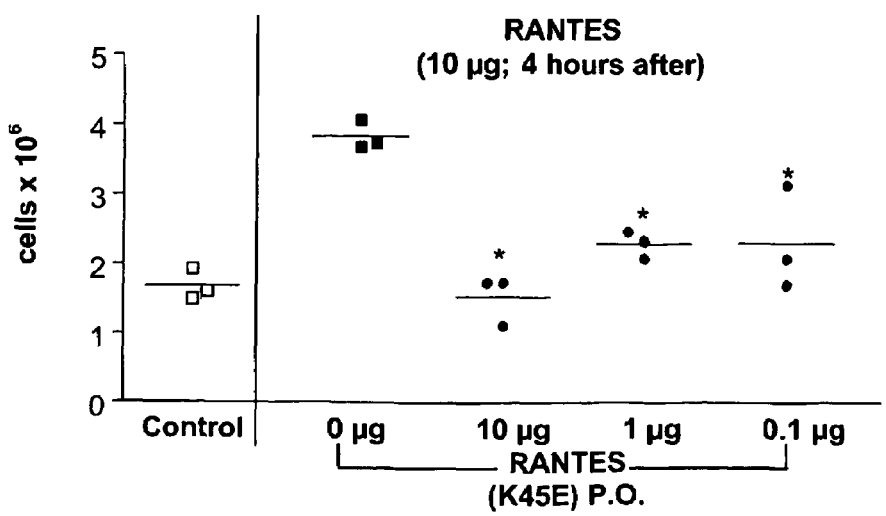

This application is the U.S. national stage application of International Patent Application No. PCT/EP03/50084, filed Mar. 31, 2003, which claims priority to European Patent Application Number 02100339.7, filed Apr. 4, 2002.

FIELD OF THE INVENTION

The present invention relates to the administration by the oral route of muteins of chemokines, such as RANTES and MIP-1beta, for treating or preventing autoimmune and inflammatory diseases as well as bacterial and viral infections.

BACKGROUND OF THE INVENTION

Chemokines are secreted pro-inflammatory proteins of small dimensions (70-130 amino acids) mostly involved in the directional migration and activation of cells, especially the extravasation of leukocytes from the blood to tissue localizations needing the recruitment of these cells (Baggiolini M et al., 1997; Rossi D and Zlotnik A, 2000; Fernandez E J and Lolis E, 2002). Usually chemokines are produced at the site of an injury, inflammation, or other tissue alteration in a paracrine or autocrine fashion, triggering cell-type specific migration and activation.

Depending on the number and the position of the conserved cysteines in the sequence, chemokines are classified into C, C—C, C—X—C and C—$X_3$—C chemokines. Inside each of these families, chemokines can be further grouped according to the sequence homology of the entire sequence and/or specific activities. Many C—X—C chemokines such as interleukin-8 (IL-8) are chemotactic for neutrophils, while C—C chemokines are active on a variety of leukocytes including monocytes, lymphocytes, eosinophils, basophils, NK cells and dendritic cells.

A series of heptahelical, G-protein coupled, membrane receptors are the binding partners that allow chemokines to exert their biological activity on the target cells, which present specific combinations of receptors according to their state and/or type. An unified nomenclature for chemokine ligands and receptors, which were originally named by the scientists discovering them in a very heterogeneous manner, has been proposed to associate each of these molecule to a systemic name including a progressive number: CCL1, CCL2, etc. for C—C chemokines; CCR1, CCR2, etc. for C—C chemokines receptors, and so on.

The physiological effects of chemokines result from a complex and integrated system of concurrent interactions. The receptors often have overlapping ligand specificity, so that a single receptor can bind different chemokines, as well a single chemokine can bind different receptors.

Even though there are potential drawbacks in using chemokines as therapeutic agents (tendency to aggregate, promiscuous binding), these molecules offer the possibility for therapeutic intervention in pathological conditions associated to such processes, in particular by inhibiting/antagonizing specific chemokines and their receptors at the scope to preventing the excessive recruitment and activation of cells, in particular leukocytes, for a variety of indications related to inflammatory and autoimmune diseases, cancers, and bacterial or viral infections (Baggiolini M, 2001; Godessart N and Kunkel S L, 2001; Proudfoot A et al., 2000).

In particular, the N-terminal domain of chemokines is involved in receptor binding and N-terminal domain processing can either activate chemokines or render chemokines completely inactive. Amino-terminal variants of synthetic C—C chemokines have been tested for their activity as inhibitors or antagonists of the naturally occurring forms. MCP-1, MCP-3 and RANTES missing up to 8 or 9 N-terminal amino acids are inactive on monocytes and are useful as receptor antagonists in the therapy and/or in diagnosis of the diseases, in which an antagonistic activity of the chemokine effects is required (Gong J H et al., 1995; Gong J H et al., 1996; WO 99/16877). Alternatively, extension of RANTES with a methionine results in almost complete inactivation of the molecule, called Met-RANTES, which behaves as an antagonist for the authentic one (Proudfoot A E et al., 1996).

Even if the chemoattractant activity of RANTES and of CC chemokines in general has been studied mainly in connection with the specific cell membrane receptors, RANTES can interact also with Glycosaminoglycans (GAGs), highly variable, branched sugar groups added post-translationally to several proteins, generically called proteoglycans (PGs). Such proteins are present on cell membrane, in the extracellular matrix and in the blood steam, where isolated GAGs can also be present.

The interaction with GAGs is a feature common to many cell-signaling soluble molecules (interleukins, growth factors). PGs, or isolated GAGs, can form a complex with soluble molecules, probably at the scope to protect this molecule from proteolysis in the extracellular environment. It has been also proposed that GAGs may help the correct presentation of cell signaling molecules to their specific receptor and, eventually, also the modulation of target cell activation.

In the case of chemokines, the concentration into immobilized gradients at the site of inflammation and, consequently, the interaction with cell receptors and their activation state seem to be modulated by the different forms of GAGs (Hoogewerf A J et al., 1997). Therefore, it has been suggested that the modulation of such interactions may represent a therapeutic approach in inflammation and other diseases (Schwarz M K and Wells T N, 1999).

The structural requirements and functional effects of GAG-RANTES interaction have been studied in various models. RANTES binds GAGs on human umbilical vein endothelial cells (HUVECs) at micromolar concentrations with an affinity and a specificity higher then other chemokines, like MCP-1, IL-8, or MIP-1alpha. Such interaction appears to be not simply electrostatic but also depending by other parameters like length and N- and O-sulphation of the GAGs (Kuschert G S et al., 1999). GAG-defective cell lines still can bind chemokines but the presence of cell surface GAGs greatly enhances their activity on the receptors when they are at low concentrations (Ali S et al., 2000).

RANTES contains a cationic sequence composed of a dibasic site, separated by a residue to another basic residue (RKNR) at residues 44-47, which is conserved in other chemokines, like MIP-1alpha (Koopmann W and Krangel M S, 1997) and MIP-1beta (Koopmann W et al., 1999). Human RANTES variants containing single mutations in this cationic sequence have been disclosed as RANTES antagonists having potential therapeutic applications in the treatment of HIV infection and inflammatory or allergic diseases (WO 99/33989). In particular, a triple mutant of RANTES, in which three residues at positions 44, 45 and 47 have been substituted with Alanine, has lost the GAG-binding ability and it is useful in the treatment of multiple sclerosis and/or other demyelinating diseases (WO 02/28419).

Several peptides and proteins, which have become commercialized drug products, lack oral efficacy and therefore have always been administered by parenteral route. Injections are generally performed by the physician or by the medical professional staff and the patients are expected to visit a surgery or a hospital regularly in order to receive treatment. Besides the discomfort created, the time taken up by this type of application often leads to unsatisfactory compliance by the patient, particularly when the treatment extends over several months.

SUMMARY OF THE INVENTION

It has been surprisingly found that C—C chemokine mutants in the 40's conserved dibasic site can exert their therapeutic activity for a longer time when administered orally. Therefore, it appears that the oral administration of chemokine-based therapeutic proteins can be improved by simply mutating this specific basic site, thus rendering possible the self-administration by the patient and consequently improving patients' cooperation and compliance. Additional advantages will become evident from the description, which follows.

DESCRIPTION OF THE FIGURES

FIG. 1: dose response curve of RANTES variants mutated in the 40's conserved dibasic site, showing the blocking effect on RANTES-induced peritoneal cell recruitment. RANTES (R44AK45AR47A) is administered I.P. (FIG. 1A) or P.O. (FIG. 1B). RANTES(K45E) is administered P.O. (FIG. 1C). Doses providing a statistically significant effect are indicated with *.

FIG. 2: time course of the blocking effect of a RANTES variant mutated in the 40's conserved dibasic site on RANTES-induced peritoneal cell recruitment. RANTES (R44AK45AR47A) is administered I.P. (FIG. 2A) or P.O. (FIG. 2B). Doses providing a statistically significant effect are indicated with *.

FIG. 3: blocking effect on MIP-1beta-induced peritoneal cell recruitment of a MIP-1beta variant mutated in the 40's conserved dibasic site, MIP-1beta (K45AR46AK48A), when administered orally (P.O.). Doses providing a statistically significant effect are indicated with *.

FIG. 4: effect of P.O. or I.P. administration of RANTES (R44AK45AR47A) on the clinical score in the murine EAE mouse model, compared with controls and IFNbeta.

DETAILED DESCRIPTION OF THE INVENTION

The main object of the present invention is the use of a mutant C—C chemokine chosen amongst RANTES, MIP-1alpha, MIP-1beta and their muteins having at least 90% homology with the corresponding wild-type (WT) molecule, to produce a pharmaceutical composition for treating or preventing autoimmune and inflammatory diseases, as well as bacterial and viral infections by oral administration, wherein said mutant comprises at least one non-conservative mutation in the 40's dibasic site. The 40's cationic sequence containing this dibasic site common to some C—C chemokines is clearly identified in WO 02/28419 (see in particular FIG. 1).

Even though the possibility to administrate C—C chemokines by oral route has been evoked (U.S. Pat. Nos. 6,214,540; 5,965,697), there is no evidence in the literature that the bioavailbility of chemokines results improved by the elimination of the 40's conserved dibasic site involved in GAGs binding.

Therefore, the oral administration of C—C chemokine-based therapeutic proteins can be advantageously provided by simply mutating a specific dibasic site, making more acceptable the use of such therapeutic proteins in the case of a long-term therapy, such as the ones of chronic inflammatory and autoimmune diseases. Another advantage of the oral administration lies in a substantially lower complications' rate due to possible side effects, such as local inflammation, abscess formation and nerve lesions, which can be observed in cases of injections.

The C—C chemokines mutants in the 40's conserved dibasic site that have been shown to be orally bioavailable are in particular the ones of RANTES, MIP-1alpha, MIP-1beta as well as their muteins having at least 90% homology with the corresponding wild-type (WT) molecule, preferably having from 95 to 99% of homology. This definition includes the muteins of these proteins being modified and/or shortened at level of N-/C-terminal domain (e.g. AOP-RANTES, or muteins having 1 or 2 amino acid deletion or extension at the N-terminus).

Some examples of these muteins include all the muteins, which comprise at least one non-conservative mutation with respect to WT molecule in the 40's conserved dibasic site associated to the GAG-binding domain and that, by the means of this mutation may have a reduced GAG-binding activity. Indeed these muteins are the preferred ones according to the invention.

The wording "a reduced GAG-binding activity" means that the mutants of the invention have a lower ability to bind to GAGs, i.e. a lower percentage of each of these mutants bind to GAGs (like heparin sulphate) with respect to the corresponding wild-type molecule.

More preferably are mutants of human RANTES, in which the at least one basic amino acids at positions 44 and 45 of the wild-type molecule have been substituted by other amino acids. An additional non-conservative substitution can be provided in position 47, the other basic residue forming the GAG-binding domain of RANTES. Such residues can be substituted with small, aliphatic, non-polar or slightly polar residues (Ala, Ser, Thr, Pro, Gly) or with residues having opposite polarity (Asp, Glu). Alanine and glutammic acid the preferred one.

Some examples of the muteins included in the definition of the invention are those comprising an amino acid sequence selected from the group consisting of SEQ ID NO: 1, 2, 3, 4, 5, 6, 7, 8 and 9. More preferably these mutated C—C chemokines comprise an amino acid sequence selected from the group consisting of SEQ ID NO: 1, 5 and 9.

Therefore the main object of the present invention is the use of the RANTES, MIP-1alpha, MIP-1beta as well as their muteins having at least 90% homology with the corresponding wild-type (WT) molecule to produce a pharmaceutical composition for treating or preventing autoimmune and inflammatory diseases as well as bacterial and viral infections by oral administration. Non-limitative examples of such diseases are the following: arthritis, rheumatoid arthritis (RA), psoriatic arthritis, osteoarthritis, systemic lupus erythematosus (SLE), systemic sclerosis, scleroderma, polymyositis, glomerulonephritis, liver/skin/lung fibrosis, allergic or hypersensitvity diseases, dermatitis, Type IV hypersensitivity also called delayed-type hypersensitivity or DTH, asthma, chronic obstructive pulmonary disease (COPD), inflammatory bowel disease (IBD), Crohn's diseases, ulcerative colitis, multiple sclerosis, septic shock, HIV-infection, transplantation, graft-versus-host disease (GVHD).

The chemokine mutants as defined above can be included in fusion proteins with heterologous sequences, which may provide additional properties without significantly impairing the activities of the chemokine mutants. Examples of such additional properties are an easier purification procedure, a longer lasting half-life in body fluids, or extracellular localization. This latter feature is of particular importance for defining a specific group of fusion or chimeric proteins included in the above definition since it allows the chemokine mutants to be localized in the space where not only where the isolation and purification of these peptides is facilitated, but also where chemokines naturally interact.

Additional protein sequences which can be comprised in fusion proteins including the chemokine mutants of the Invention can be chosen amongst membrane-bound proteins, extracellular domains of membrane-bound protein, immunoglobulin constant region, multimerization domains, extracellular proteins, signal peptide-containing proteins, export signal-containing proteins. Alternatively, the heterologous sequence can be helpful for purification by affinity (Lowe C R et al., 2001).

The choice of one or more of these sequences to be fused to the chemokine mutant is functional to specific use of said agent. As a general procedure, these fusion proteins can be produced by generating nucleic acid segments encoding them, using common genetic engineering techniques, and cloning in replicable vector of viral or plasmid origin which are used to modify a Prokaryotic or Eukaryotic host cell, using episomal or non-/homologously integrated vectors, as well as transformation-, infection-, or transfection-based technologies. These vectors should allow the expression of the fusion protein in the prokaryotic or eukaryotic host cell under the control of their own transcriptional initiation/termination regulatory sequences, which are chosen to be constitutively active or inducible in said cell. A cell line substantially enriched in such cells can be then isolated to provide a stable cell line.

The chemokine mutants can be in alternative forms which can be preferred according to the desired method of use and/or production, for example as active fractions, precursors, salts, or derivatives.

The term "fraction" refers to any fragment of the polypeptidic chain of the compound itself, alone or in combination with related molecules or residues bound to it, for example residues of sugars or phosphates, or aggregates of the original polypeptide or peptide. Such molecules can result also from other modifications which do not normally alter primary sequence, for example in vivo or in vitro chemical derivativization of peptides (acetylation or carboxylation), those made by modifying the pattern of phosphorylation (introduction of phosphotyrosine, phosphoserine, or phosphothreonine residues) or glycosylation (by exposing the peptide to enzymes which affect glycosylation e.g., mammalian glycosylating or deglycosylating enzymes) of a peptide during its synthesis and processing or in further processing steps.

The "precursors" are compounds which can be converted into the compounds of present invention by metabolic and enzymatic processing prior or after the administration to the cells or to the body.

The term "salts" herein refers to both salts of carboxyl groups and to acid addition salts of amino groups of the peptides, polypeptides, or analogs thereof, of the present invention. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid. Any of such salts should have substantially similar activity to the peptides and polypeptides of the invention or their analogs.

The term "derivatives" as herein used refers to derivatives which can be prepared from the functional groups present on the lateral chains of the amino acid moieties or on the N-/ or C-terminal groups according to known methods. Such derivatives include for example esters or aliphatic amides of the carboxyl-groups and N-acyl derivatives of free amino groups or O-acyl derivatives of free hydroxyl-groups and are formed with acyl-groups as for example alcanoyl- or aroyl-groups.

Alternatively, conjugates or complexes of the chemokine mutants can be generated using molecules and methods known in the art, for example, to improve their delivery with polyethylene glycol and other natural or synthetic polymers (Pillai O and Panchagnula R, 2001).

The chemokines mutants, and the fusion proteins containing them, can be prepared by recombinant DNA-based techniques, using vectors of viral or plasmid origin which allows the expression of the nucleic acid encoding for the chemokine mutants in prokaryotic or eukaryotic host cells transformed with such vectors.

The DNA sequence coding for the chemokine mutant can be inserted and ligated into a suitable vector. Once formed, the expression vector is introduced into a suitable host cell, which then expresses the vector(s) to yield the desired protein.

Expression of any of the recombinant proteins of the invention as mentioned herein can be effected in eukaryotic cells (e.g. yeasts, insect or mammalian cells) or prokaryotic cells, using the appropriate expression vectors. Any method known in the art can be employed.

For example the DNA molecules coding for the proteins obtained by any of the above methods are inserted into appropriately constructed expression vectors by techniques well known in the art. Double stranded cDNA is linked to plasmid vectors by homopolymeric tailing or by restriction linking involving the use of synthetic DNA linkers or blunt-ended ligation techniques: DNA ligases are used to join the DNA molecules, and undesirable joining is avoided by treatment with alkaline phosphatase.

In order to be capable of expressing the desired protein, an expression vector should also comprise specific nucleotide sequences containing transcriptional and translational regulatory information linked to the DNA coding the desired protein in such a way as to permit gene expression and production of the protein. First in order for the gene to be transcribed, it must be preceded by a promoter recognizable by RNA polymerase, to which the polymerase binds and thus initiates the transcription process. There are a variety of such promoters in use, which work with different efficiencies (strong and weak promoters).

For Eukaryotic hosts, different transcriptional and translational regulatory sequences may be employed, depending on the nature of the host. They may be derived form viral sources, such as adenovirus, bovine papilloma virus, Simian virus or the like, where the regulatory signals are associated with a particular gene which has a high level of expression. Examples are the TK promoter of the Herpes virus, the SV40 early promoter, the yeast gal4 gene promoter, etc. Transcriptional initiation regulatory signals may be selected which allow for repression and activation, so that expression of the genes can be modulated.

The DNA molecule comprising the nucleotide sequence coding for the chemokine mutants is inserted into vector(s), having the operably linked transcriptional and translational regulatory signals, which is capable of integrating the desired gene sequences into the host cell. After the introduction of the vector(s), the host cells are grown in a selective medium, which selects for the growth of vector-containing cells. Expression of the cloned gene sequence(s) results in the production of the desired proteins.

The cells that have been stably transformed by the introduced DNA can be selected by also introducing one or more markers allowing for selection of host cells containing the expression vector. The marker may also provide for phototrophy to an auxotropic host, biocide resistance, e.g. antibiotics, or heavy metals such as copper, or the like. The selectable marker gene can either be directly linked to the DNA gene sequences to be expressed, or introduced into the same cell by co-transfection.

Additional elements of the vectors may also be useful for obtaining an optimal production of proteins of the invention, in particular for selecting a particular cell containing plasmid or viral vector: the ease with which recipient cells, that contain the vector may be recognized and selected from those recipient cells which do not contain the vector; the number of copies of the vector which are desired in a particular host; and whether it is desirable to be able to "shuttle" the vector between host cells of different species.

Once the vector(s) or DNA sequence containing the construct(s) has been prepared for expression the DNA construct(s) may be introduced into an appropriate host cell by any of a variety of suitable means: transformation, transfection, conjugation, protoplast fusion, electroporation, calcium phosphate-precipitation, direct microinjection, etc.

Host cells may be either prokaryotic or eukaryotic. Preferred are eukaryotic hosts, e.g. mammalian cells, such as human, monkey, mouse, and Chinese Hamster Ovary (CHO) cells, because they provide post-translational modifications to protein molecules, including correct folding or glycosylation at correct sites. Also yeast cells can carry out post-translational peptide modifications including glycosylation. A number of recombinant DNA strategies exist which utilize strong promoter sequences and high copy number of plasmids that can be utilized for production of the desired proteins in yeast. Yeast recognizes leader sequences on cloned mammalian gene products and secretes peptides bearing leader sequences (i.e., pre-peptides).

Specific descriptions of methods for preparing RANTES mutants are provide d WO 02/28419 and to EP 01000761.5 (both applications in the Examples' sections report complete and specific methods for the recombinant preparation of all the muteins cited herein). The preparation of the muteins of MIP-1alpha and MIP-1beta has been disclosed in the literature (Koopmann W and Krangel M S., 1997; Laurence J S et al., 2001). Moreover, many reviews (Makrides S C, 1999) and books provide teachings on how to clone and produce recombinant proteins using vectors and Prokaryotic or Eukaryotic host cells, such as some titles in the series "A Practical Approach" published by Oxford University Press ("DNA Cloning 2: Expression Systems", 1995; "DNA Cloning 4: Mammalian Systems", 1996; "Protein Expression", 1999; "Protein Purification Techniques", 2001).

Alternatively, the chemokines mutants, and the fusion proteins containing them, can be prepared by chemical synthesis technologies, such as solid phase synthesis and liquid phase synthesis. Given the short length, totally synthetic chemokines can be generated (Brown A et al., 1996). As a solid phase synthesis, for example, the amino acid corresponding to the C-terminus of the peptide to be synthetized is bound to a support which is insoluble in organic solvents, and by alternate repetition of reactions, one wherein amino acids with their amino groups and side chain functional groups protected with appropriate protective groups are condensed one by one in order from the C-terminus to the N-terminus, and one where the amino acids bound to the resin or the protective group of the amino groups of the peptides are released, the peptide chain is thus extended in this manner.

Solid phase synthesis methods are largely classified by the tBoc method and the Fmoc method, depending on the type of protective group used. Typically used protective groups include tBoc (t-butoxycarbonyl), Cl-Z (2-chlorobenzyloxycarbonyl), Br-Z (2-bromobenzyloxycarbonyl), Bzl (benzyl), Fmoc (9-fluorenylmethoxycarbonyl), Mbh (4,4'-dimethoxydibenzhydryl), Mtr (4-methoxy-2,3,6-trimethylbenzenesulphonyl), Trt (trityl), Tos (tosyl), Z (benzyloxycarbonyl) and Cl2-Bzl (2,6-dichlorobenzyl) for the amino groups; NO2 (nitro) and Pmc (2,2,5,7,8-pentamethylchromane-6-sulphonyl) for the guanidino groups); and tBu (t-butyl) for the hydroxyl groups). After synthesis of the desired peptide, it is subjected to the de-protection reaction and cut out from the solid support. Such peptide cutting reaction may be carried with hydrogen fluoride or tri-fluoromethane sulfonic acid for the Boc method, and with TFA for the Fmoc method.

The chemokine mutants obtained by recombinant DNA or chemical synthesis technologies are finally subjected to one or more steps of purification. Purification can be carried out by any one of the methods known for this purpose, i.e. any conventional procedure involving extraction, precipitation, chromatography, electrophoresis, or the like. For example, HPLC (High Performance Liquid Chromatography) can be used. The elution can be carried using a water-acetonitrile-based solvent commonly employed for protein purification.

Another object of the present invention is, therefore, the method for treating or preventing any of the above mentioned diseases by administering an effective amount of mutant C—C chemokine chosen amongst RANTES, MIP-1alpha, MIP-1beta and their muteins having at least 90% homology with the corresponding wild-type (WT) molecule, wherein said mutant comprises at least one non-conservative mutation in the 40's dibasic site, together with a pharmaceutically acceptable excipient.

Another embodiment of the present invention is the method for treating MS and/or other demyelinating diseases by orally administering an effective amount of mutant C—C chemokine chosen amongst RANTES, MIP-1alpha, MIP-1beta and their muteins having at least 90% homology with the corresponding wild-type (WT) molecule, wherein said mutant comprises at least one non-conservative mutation in the 40's dibasic site, together with a pharmaceutically acceptable excipient.

The chemokines of the present invention can be administered to a patient in need, alone, or in pharmaceutical compositions where one or more of the chemokines are mixed with suitable carriers or pharmaceutically acceptable excipient(s) at doses to treat, ameliorate or prevent the disease.

The pharmaceutical composition may comprise other active ingredients in addition to the chemokines or the treatment with the chemokines may be combined with the treatment with other active ingredients, which are able to treat, ameliorate or prevent the same disease.

A "therapeutically effective" dose further refers to that amount of the compound sufficient to result in amelioration of symptoms. Techniques for formulation and administration of the compounds of the instant application may be found in "Remington's Pharmaceutical Sciences," Mack Publishing Co., Easton, Pa., latest edition.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active molecules into preparations which can be used pharmaceutically.

For example, for oral administration, the active ingredient can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations, which can be used orally, include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein. The exact formulation and dosage can be chosen by the individual physician in view of the patient's condition. See, e.g., Fingl et al., 1975, in "The Pharmacological Basis of Therapeutics", Ch. 1.

Preferably, the dosage of the chemokines of the present invention as defined above is between about 10 µg to about 100 mg a day, more preferably from 0.05 to 10 mg per day. Moreover, the age, sex and physical condition of the patient, as well as other concurrent treatments being administered also have a bearing on the effective dosage of the chemokines for treatment. Consequently, adjustment and refinement of the dosages used and administration schedules must be determined based on these factors, and may need to be determined experimentally. Such determinations, however, require no more than routine experimentation.

It will be appreciated that unit content of active ingredient(s) contained in an individual dose of each dosage form need not in itself constitute an effective amount, since the necessary effective amount can be reached by administration of a plurality of dosage units (such as capsules or tablets or combinations thereof. Administration of an effective dosage may be in a single dose form or in multiple dosage forms and it may be provided with an enteric coating and/or a sustained release mechanism, such as a degradable matrix or a reservoir.

The compositions may, if desired, be presented in a pack or dispenser device that may contain one or more unit dosage forms containing the active ingredient. The pack may, for example, comprise metal or plastic foil, such as a blister pack. The pack or dispenser device may be accompanied by instructions for administration.

Compositions comprising a compound of the invention formulated in a compatible pharmaceutical carrier may also be prepared, placed in an appropriate container, and labeled for treatment of an indicated condition. Suitable conditions indicated on the label may include treatment of disorders or diseases in which the administration of a compound of the present invention is desired to ameliorate either the disease or disorder or symptoms related to such disease or disorder.

"Oral" administration includes oral, enteral or intragastric administration. In addition, synergists can be conjoined in the treatment to enhance the effectiveness of the above.

All references cited herein are entirely incorporated by reference herein, including all data, tables, figures, and text presented in the cited references. Additionally, the entire contents of the references cited within the references cited herein are also entirely incorporated by reference. Reference to known method steps, conventional method steps, known methods or conventional methods is not in any way an admission that any aspect, description or embodiment of the present invention is disclosed, taught or suggested in the relevant art.

Once understood the features of the methods and products disclosed in present application, the necessity and kind of additional steps can be easily deduced by reviewing prior art. The following are examples, which are intended to illustrate the present invention without limiting its scope. Table 1 clarifies the identity of the sequences reported in the Sequence Listing and throughout the text.

EXAMPLES

Methods

Pharmacokinetic (PK) Study

Female Balb/c mice aged 8-12 weeks were dosed with 5 mg/kg of human RANTES or RANTES(R44AK45AR47A) by oral route (P.O.; oral gavage). Blood was sampled at various time points (n=3 mice per group), serum was collected and the PK profile of the mutant chemokine was obtained by ELISA, using a polyclonal anti-human RANTES antibody pair (Pharmingen 20581D/20582D), which was set up in house to detect human RANTES or human RANTES(R44AK45AR47A) and not endogenous mouse RANTES.

Peritoneal Cell Chemotaxis

Female Balb/c mice aged 8-12 weeks were pre-dosed 4 hours P.O. (oral adminstration by oral gavage) or 30 minutes I.P. (intraperitoneally) with 200 µl vehicle control (NaCl), of the wild type (WT) or the chemokine mutant. At t=0, mice were dosed I.P. with 200 µl vehicle control (NaCl), WT or mutant chemokine. Mice were sacrificed 18 hours later, a peritoneal lavage was performed and total cells collected counted using a haemocytometer.

Statistical Analysis

Total cell counts from peritoneal lavage are expressed as individual counts with the mean of the group. Statistical significance was calculated using a one-way ANOVA with Bonferroni post test by GraphPad (version 3.0; Prism software). A value p<0.05 calculated in this way indicates a statistically significant difference in the effect provided by a protein or a dose (represented with * in the figures).

Experimental Autoimmune Encephalomyelitis (EAE)

Immunization was applied on 8-week old C57 BL/6NCrIBR female mice weighing 18-22 grams by injecting 0.1 ml of an emulsion containing 200 µg myelin oligodendrocyte glycoprotein 33-35 ($MOG_{35-55}$) peptide (Neosystem) in Complete Freund's Adjuvant (CFA, with *Mycobacterium butyricum*; Difco) containing 0.25 mg of *Mycobacterium tuberculosis* (day=0; subcutaneous injection in the back of the neck). Before the s.c injection, they received a 200 µl intravenous injection of 300 ng pertussis toxin (List Biological Lab.) dissolved in phosphate-buffered saline (PBS) in the tail vein. On day 2 the animals were given a second intraperitoneal injection of 300 ng of pertussis toxin in PBS. This procedure results, starting approximately from day 8-10, in the appearance of a progressive paralysis, arising from the tail and progressively ascending up to the forelimbs.

The study involved five groups of 10 animals, all immunized with $MOG_{35-55}$ peptide in CFA and pertussis toxin, which treated as follows:

Group 1: positive control group dosed with vehicle alone (200 µl PBS) by I.P. route.
Group 2: positive control group dosed with vehicle alone (200 µl PBS) by P.O. route.
Group 3: 200 µl/mouse of PBS dosed with 10 µg/mouse I.P. of RANTES (R44AK45AR47A)
Group 4: 200 µl/mouse of PBS dosed with 100 µg/mouse p.o. of RANTES (R44AK45AR47A)
Group 5: 200 µl/mouse of PBS dosed with 20,000 U/mouse S.C. (subcutaneously) of mouse recombinant interferon beta (IFNbeta)

The treatment started for each animal at experimental day 7 (approximately 3 days before the usual occurrence of the disease) and then continued for 21 consecutive days. Animals were then sacrificed at experimental day 28.

Starting from day 5 the animals were individually examined for the presence of paralysis by means of a clinical score as follows:
0=no sign of disease
0.5=partial tail paralysis
1=tail paralysis
1.5=tail paralysis+partial unilateral hindlimb paralysis
2=tail paralysis+hindlimb weakness or partial hindlimb paralysis
2.5=tail paralysis+partial hindlimb paralysis (lowered pelvi)
3=tail paralysis+complete hindlimb paralysis
3.5=tail paralysis+complete hindlimb paralysis+incontinence
4=tail paralysis+hindlimb paralysis+weakness or partial paralysis of forelimbs
5=moribund or dead.

Results

Detection of RANTES(R44AK45AR47A) in Serum Following P.O. Administration

Both RANTES (SEQ ID NO: 10) and RANTES (R44AK45AR47A) (SEQ ID NO: 1) are detected in the serum following oral administration. In particular, RANTES (R44AK45AR47A), when administered P.O at a dose of 100 µg/mouse, is detected in the serum of the animals by ELISA at a peak level of 5.86 ng/ml serum 4 hours after P.O. administration (Table 2; nd=not detected). This peak is, obviously, delayed when compared to other administration systems (intravascular or intraperitoneal), wherein the peak is obtained at 30 minutes.

Figure 2:
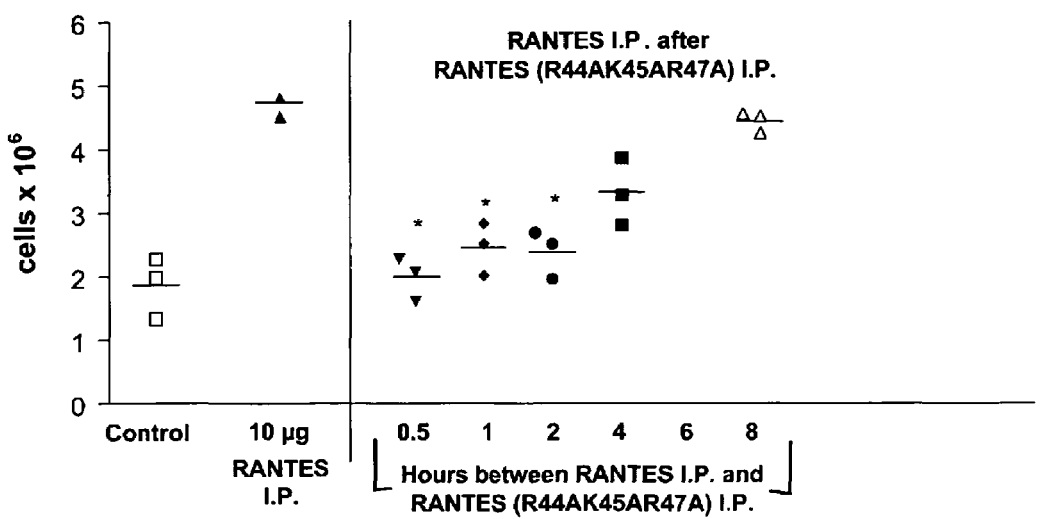
Figure 2:
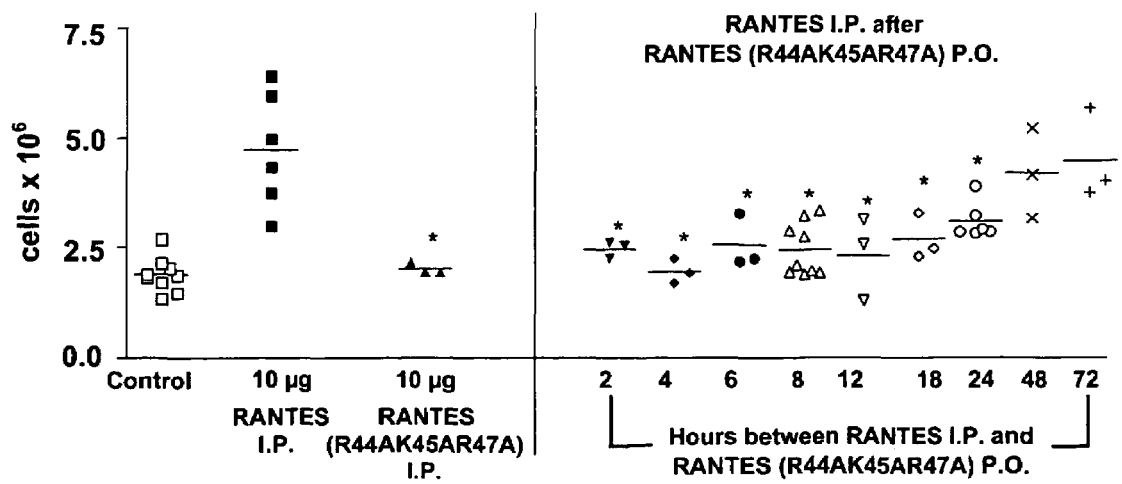

Oral Administration of C—C Chemokines Mutants in RANTES-induced Peritoneal Cell Recruitment Mice were pre-dosed I.P. with RANTES, which increases the yield of peritoneal cells by approximately 2-fold compared with baseline. RANTES(R44AK45AR47A) fails to recruit cells, if administered intraperitoneally, but it is active as antagonist of RANTES if administered intraperitoneally as well (FIG. 2A). A dose dependent inhibition of RANTES-induced recruitment was observed also when the mutants RANTES(R44AK45AR47A) and RANTES(K45E) (SEQ ID NO: 5) are administered orally (FIGS. 2B and 2C).

The time course of RANTES(R44AK45AR47A) when administered intraperitoneally (FIG. 2A) or orally (FIG. 2B) show that RANTES(R44AK45AR47A) was effective at inhibiting cell recruitment up to 24 hour before RANTES when administered orally, that is a longer time if compared to the intraperitonal administration. Thus, mutations in the dibasic site improve chemokine bioavailability.

Figure 3:
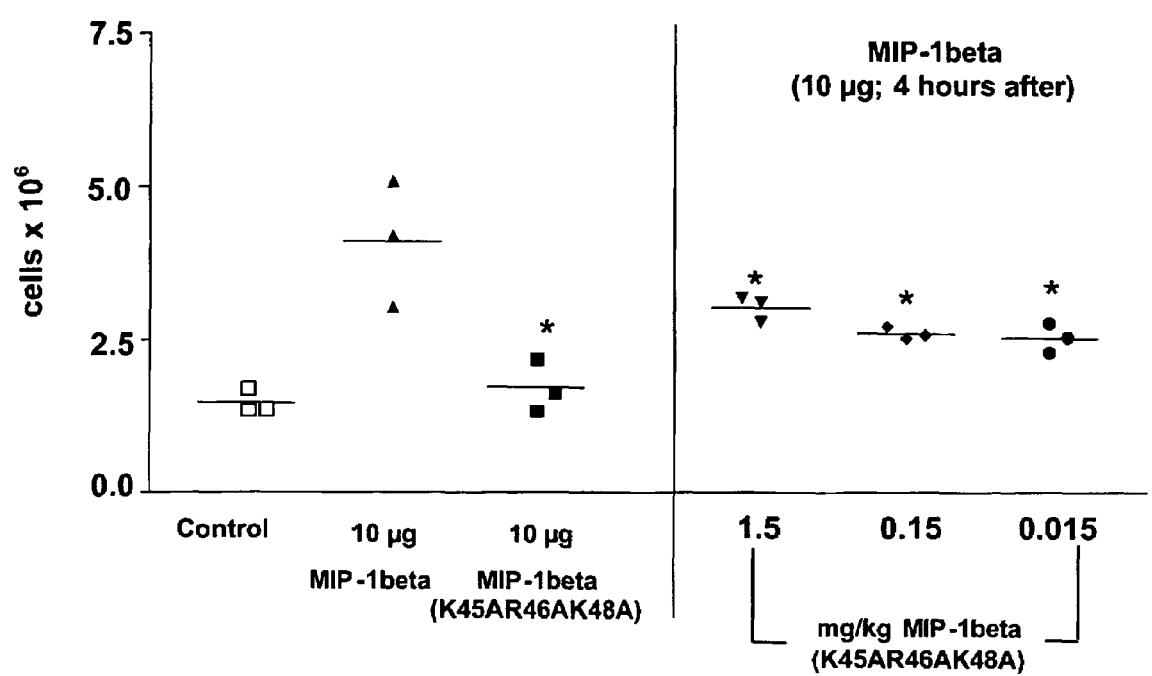

As shown for the corresponding RANTES mutant, MIP-1beta(K45AR46AK48A) (SEQ ID NO: 9) effectively inhibits MIP-1beta-induced cell recruitment at doses as low as 0.015 mg/kg (FIG. 3).

Figure 4:
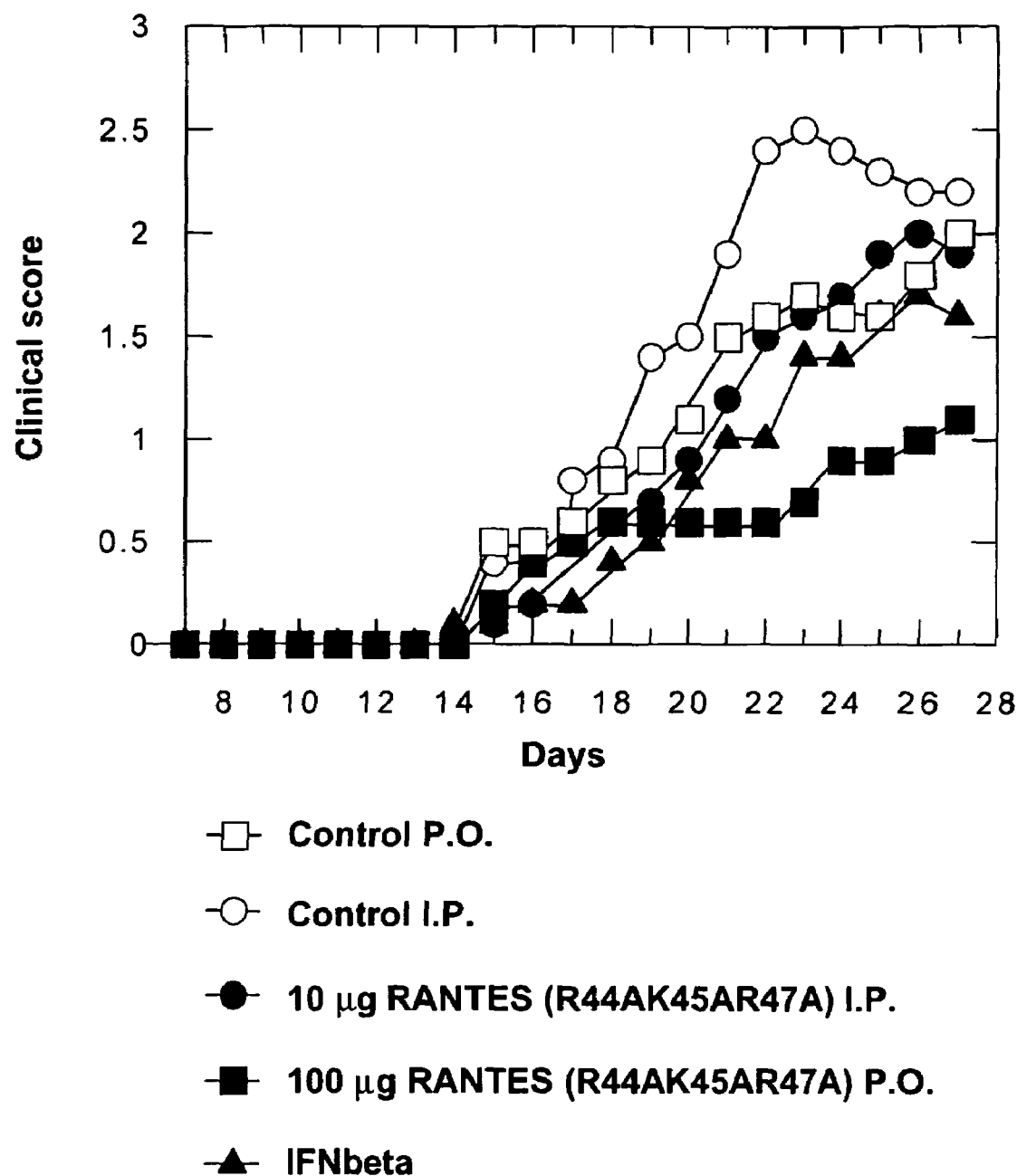

Oral vs. Intraperitoneal Efficacy of RANTES (R44AK45AR47A) in the Murine EAE Model RANTES(R44AK45AR47A) shows a beneficial effect in the murine EAE model for multiple sclerosis when administered orally. The protein, at 100 µg/mouse administered daily P.O. demonstrated a better efficacy than the reference treatment (recombinant mouse IFN-beta). The mean of the maximum clinical score reached during the experiment was also decreased (FIG. 4). These results show a clear beneficial effect of the oral administration of RANTES (R44AK45AR47A), which reduces clinical signs of chronic EAE in mice after immunization with MOG. Therefore, RANTES(R44AK45AR47A) can be administered orally for the treatment or prevention, in chronic demyelinating diseases such as MS.

Non-conservative substitutions in the 40's dibasic site in C—C chemokines provides protein variants which, beyond the reduced GAG binding properties and the antagonistic properties, show a specific profile of activity when administered orally, since their effects are exerted for a longer time in chemokine-related disease models.

Examples of wild type and mutated C—C chemokines whose oral availability can be improved according to this invention are listed as SEQ ID NO: 10, 11, 12, 13, 14, and 15. Examples of the mutated sequences which can be used according to this invention are listed as SEQ ID NO: 1, 2, 3, 4, 5, 6, 7, 8, and 9 (Table 1).

TABLE 1

| SEQ ID NO: | Sequence description |
|---|---|
| 1 | RANTES(R44AK45AR47A) |
| 2 | RANTES(R44AK45AR47A)truncated(3-68) |
| 3 | Met-RANTES(R44AK45AR47A) |
| 4 | RANTES(G32NR44AK45AR47A) |
| 5 | RANTES(K45E) |
| 6 | Met-RANTES(G32N) |
| 7 | RANTES(G32N)truncated(3-68) |
| 8 | MIP-1alpha(R18AR46AR48A) |
| 9 | MIP-1beta(K45AR46AK48A) |
| 10 | RANTES |
| 11 | Met-RANTES |
| 12 | RANTES(3-68) |
| 13 | RANTES(G32N) |
| 14 | MIP-1alpha |
| 15 | MIP-1beta |

TABLE 2

| | RANTES (R44AK45AR47A) ng/ml in serum | | |
|---|---|---|---|
| Time post p.o. | Mouse 1 | Mouse 2 | Mouse 3 |
| 15 min | 0.58 | Nd | Nd |
| 30 min | nd | Nd | Nd |
| 1 h | nd | Nd | 2.34 |
| 2 h | 3.81 | 1.11 | 0.01 |
| 4 h | 3.17 | 5.18 | 9.24 |
| 8 h | 1.06 | 1.35 | 4.9 |

REFERENCES

Ali S et al., J Biol Chem, 275: 11721-7, 2000.

Baggiolini M et al., Annu Rev Immunol, 15: 675-705, 1997.

Baggiolini M, J Intern Med, 250: 91-104, 2001.

Brown A et al., J Pept Sci, 2: 40-46, 1996.

Fernandez E J and Lolis E, Annu Rev Pharmacol Toxicol, 42:469-499, 2002.

Godessart N and Kunkel S L, Curr Opin Immunol, 13: 670-675, 2001.

Gong J H and Clark-Lewis I, J Exp Med 181: 631-640, 1995.

Gong J H et al., J Biol Chem, 271: 10521-7, 1996.

Hoogewerf A J et al., Biochemistry, 36: 13570-8, 1997.

Koopmann Wand Krangel M S, J. Biol. Chem, 272: 10103-9, 1997.

Koopmann Wet al., J Immunol, 163: 2120-7, 1999.

Kuschert G S et al., Biochemistry, 38: 12959-68, 1999.

Laurence J S et al., Biochemistry, 40: 4990-4999, 2001.

Lowe C R et al., J Biochem Biophys Methods, 49(1-3):561-74, 2001.

Proudfoot A E et al., J Biol Chem, 271: 2599-603, 1996.

Proudfoot A et al., Immunol Rev, 177: 246-56, 2000.

Rossi D and Zlotnik A, Annu Rev Immunol, 18:217-42 2000.

Schwarz M K and Wells T N, Curr Opin Chem Biol, 3: 407-17, 1999.

The invention claimed is:

1. A method of treating multiple sclerosis comprising orally administering, to an individual, a composition comprising a pharmaceutically acceptable excipient and a RANTES polypeptide comprising SEQ ID NO:1 or amino acids 1-68 of SEQ ID NO: 1 in an amount effective to treat said individual.

2. The method of claim 1, wherein said RANTES polypeptide comprises SEQ ID NO: 1.

3. The method of claim 1, wherein said RANTES polypeptide comprises amino acids 1-68 of SEQ ID NO:1.

* * * * *